United States Patent [19]
Beussink et al.

[11] Patent Number: 5,519,984
[45] Date of Patent: May 28, 1996

[54] METHODS FOR PACKAGING A PRESSURE OR VACUUM SENSITIVE PRODUCT

[75] Inventors: Donald R. Beussink; Ronald W. Hagen, both of St. Charles, Mo.

[73] Assignee: Mallinckrodt Medical, Inc., St. Louis, Mo.

[21] Appl. No.: 405,484

[22] Filed: Mar. 16, 1995

[51] Int. Cl.⁶ .................. B65B 7/28; B67B 1/04
[52] U.S. Cl. .................................. 53/489; 53/324
[58] Field of Search .................. 53/432, 471, 489, 53/488, 281, 510, 319, 324, 330

[56] References Cited

U.S. PATENT DOCUMENTS

| | | | |
|---|---|---|---|
| 907,672 | 12/1908 | Alexander | 53/324 X |
| 1,990,301 | 2/1935 | Mora | 53/324 X |
| 2,360,423 | 10/1944 | Johnson et al. | 53/324 |
| 3,358,869 | 12/1967 | Palmer et al. | 53/489 X |
| 3,737,973 | 6/1973 | Stawski | 53/489 X |
| 4,369,570 | 1/1983 | Madden et al. | 53/319 X |
| 4,456,041 | 6/1984 | Grilli et al. | 53/324 X |
| 4,679,378 | 7/1987 | Anderson et al. | 53/489 X |
| 5,083,416 | 1/1992 | Schneider et al. | 53/489 |

*Primary Examiner*—Horace M. Culver
*Attorney, Agent, or Firm*—Thomas P. McBride

[57] ABSTRACT

Methods for packaging a pressure or vacuum sensitive product, such as an ultrasound contrast media comprised of a gas-filled microshpere or microbubble, or sealing such a product in a single-compartment syringe, in a manner that does not utilize pressure or vacuum in the process, are provided.

20 Claims, 2 Drawing Sheets

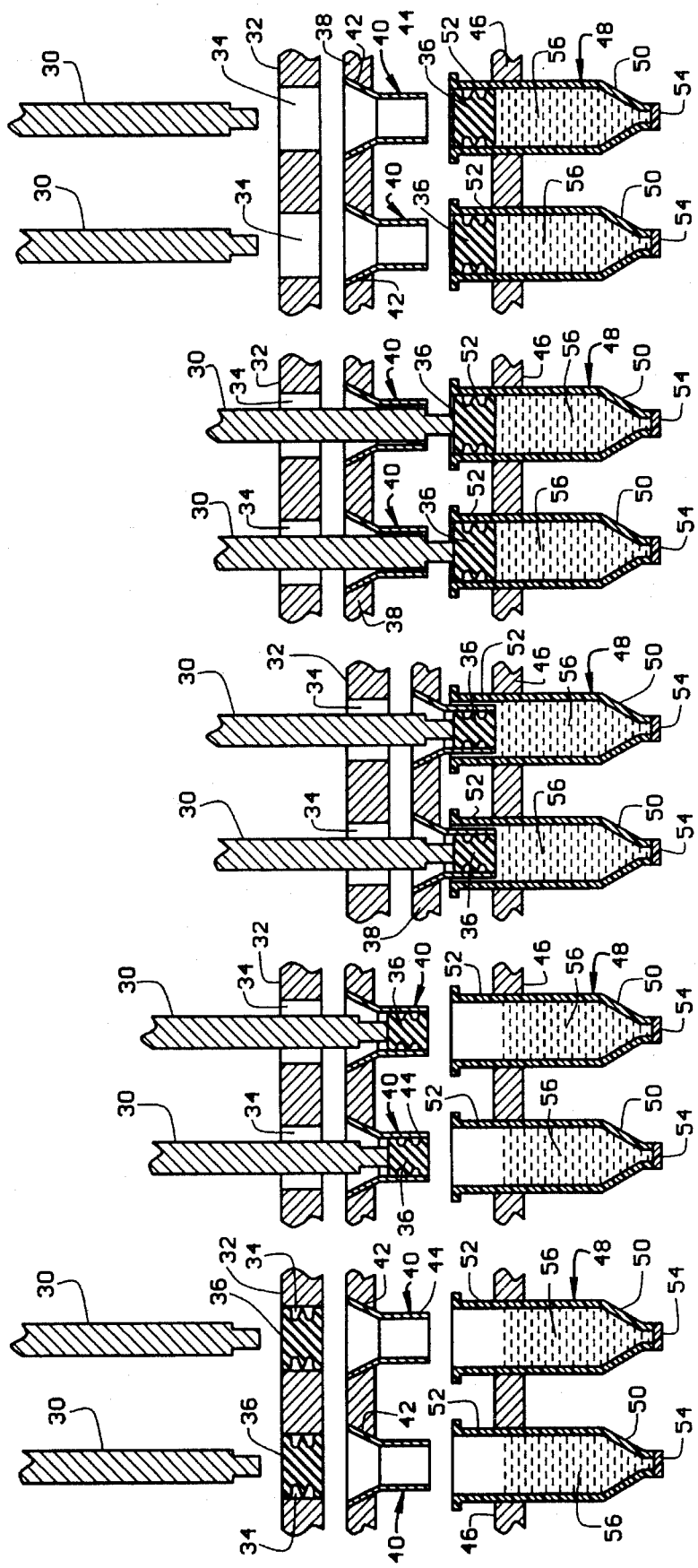

5,519,984

METHODS FOR PACKAGING A PRESSURE OR VACUUM SENSITIVE PRODUCT

FIELD OF THE INVENTION

This invention relates in general to a packaging process and, more particularly, to a method for packaging a pressure or vacuum sensitive product in a container without subjecting the product to a destructive pressure or vacuum.

BACKGROUND OF THE INVENTION

The provision of liquid pharmaceuticals in a pre-filled syringe is desirable because it eliminates manipulations required to remove the product from a conventional ampule, vial or bottle and transfer it to a syringe prior to use. Conventional processes for final assembly and sealing of pre-filled syringes, however, require the development of pressure and/or a partial vacuum in order to effectively seat the elastomeric closures which seal the product within the syringe. In one typical process, the tooled end of a syringe (the reduced diameter end that typically receives the needle) is sealed and the product filled through the large opening at the opposite end of the syringe. A partial vacuum is applied to the open end and an elastomeric closure is inserted in the syringe. When the vacuum is vented, the closure is effectively positioned within the barrel of the syringe as a result of the differential pressure existing within the syringe. As is apparent, this process results in the development of a vacuum within the syringe barrel which is detrimental to a pressure or vacuum sensitive product. In another typical process, a syringe is filled as described above, but the elastomeric closure is inserted into the barrel of the syringe with a wire or guide beside the closure. After the closure is inserted to its selected location in the syringe, the wire or guide is withdrawn. This process avoids the use of vacuum to seat the closure in the syringe, but is cumbersome and not an efficient method for large-scale production.

An alternative process for filling syringes has been developed that does not involve the development of pressure or vacuum in the syringe. In this process the large diameter end of the syringe is sealed first in a conventional manner and the liquid product is introduced through the tooled end of the syringe. The tooled end is subsequently capped with a needle or plug. This process is not preferred because the filling speed of the product through the reduced diameter end is inadequate for efficient large scale manufacturing processes.

An apparatus was developed by Becton-Dickinson, Inc. (Franklin Lakes, N.J.) for use in introducing a second closure into a two-compartment vial or syringe. This apparatus was designed to insert a closure into a syringe to seal the second compartment in a manner that did not disturb the closure sealing the first compartment. This was accomplished without pulling a vacuum or developing a pressure. It was neither known nor suggested that the apparatus could be used for packaging and/or sealing a single compartment container containing a pressure or vacuum sensitive product.

It would be desirable, therefore, to provide a method for packaging and sealing single compartment containers containing a pressure or vacuum sensitive product. Heretofore, no such method has been developed or known to the industry.

SUMMARY OF THE INVENTION

The present invention is directed to a method for packaging a pressure or vacuum sensitive product in a single-compartment container in a manner that does not utilize pressure or vacuum in the process. According to the method, in a container capable of sealing the product therein one of the ends of the container is sealed and the pressure or vacuum sensitive product introduced into the container through the other end. A compressible closure member of a normal diameter sufficient to sealingly engage the inner wall of the container is inserted into a generally conical hollow tube, the generally conical hollow tube has a first end of a diameter permitting insertion of the closure member therein and a second end of a diameter less than the diameter of the first end, such that the closure member is positioned generally within the second end of the tube and the diameter of the closure member positioned therein being correspondingly reduced. The tube containing the closure member is inserted into the container to position the closure member at a selected location within the container and a means for holding the position of the closure member substantially stationary with respect to the tube at the selected location relative to the container is provided. The tube is withdrawn from the container in a manner placing the closure member in the container such that the closure member expands and sealingly engages the inner wall of the container and the means for holding the closure member is removed.

The present invention is further directed to a method for sealing a pressure or vacuum sensitive product in a single-compartment container having one sealed end involving the introduction of the pressure or vacuum sensitive product into the container through the other end, inserting a compressible closure member of a normal diameter sufficient to sealingly engage the inner wall of the container into a generally conical hollow tube, the generally conical hollow tube having a first end of a diameter permitting insertion of the closure member therein and a second end of a diameter less than the diameter of the first end, such that the closure member is positioned generally within the second end of the tube and the diameter of the closure member positioned therein is correspondingly reduced, inserting the tube containing the closure member into the container to position the closure member at a selected location within the container, providing a means for holding the position of the closure member substantially stationary with respect to the tube at the selected location relative to the container, retracting the tube from the container in a manner placing the closure member in the container such that the closure member expands and sealingly engages the inner wall of the container, and retracting the means for holding the closure member.

Among the several advantages found to be achieved by the present invention include the provision of a method for packaging and sealing a pressure or vacuum sensitive product in a single-compartment container without the use of pressure or vacuum; the provision of such a method that is suitable for efficient, large-scale production; and the provision of a method for sealing a single-compartment container containing a pressure or vacuum sensitive product that minimizes the amount of headspace between the closure and the product. Other and further advantages of the invention will become apparent from the following description of the invention and in view of the accompanying drawing figures.

BRIEF DESCRIPTION OF THE DRAWING FIGURES

FIGS. 3–7 are cross-sectional views illustrating the steps of the methods of the invention utilizing an apparatus as in FIGS. 1 or 2.

DETAILED DESCRIPTION OF THE PREFERRED EMBODIMENTS

In accordance with the present invention, it has been discovered that containers containing a pressure or vacuum sensitive product can be packaged and sealed in a manner that does not require the use of harmful pressure or vacuum that is associated with conventional packaging and sealing procedures. As used herein, a "pressure or vacuum sensitive product" is a product whose functionality or physical or structural properties are affected by pressure or vacuum in a manner rendering the product changed or ineffective for its intended use. The methods of the present invention are particularly suitable for pressure or vacuum sensitive liquid pharmaceuticals and, more particularly, for those liquid-based pharmaceuticals comprised of microspheres, gas-filled vesicles, gas-filled liposomes, gas-filled microbubbles, or other "bubble" containing products. Moreover, the methods of the present invention are particularly suited for use in the packaging and sealing of ultrasound contrast media products including but not limited to Albunex® (Molecular Biosystems, Inc., San Diego, Calif.), an albumin based gas-filled microbubble, lipid-based gas-filled microbubbles, surfactant-based gas-filled microbubbles, polymer-based gas-filled microbubbles, liposome-based gas-filled microbubbles, phospholipid-based gas-filled microbubbles and gas-filled vesicles. Each of these products are particularly susceptible to alteration and/or damage by exposure to a pressure or vacuum. These products are provided in single-compartment containers that are aseptically filled under sterile filling conditions. The methods described herein permit these products to be filled into syringes and then sealed without exposure to pressure or vacuum.

Figure 1:
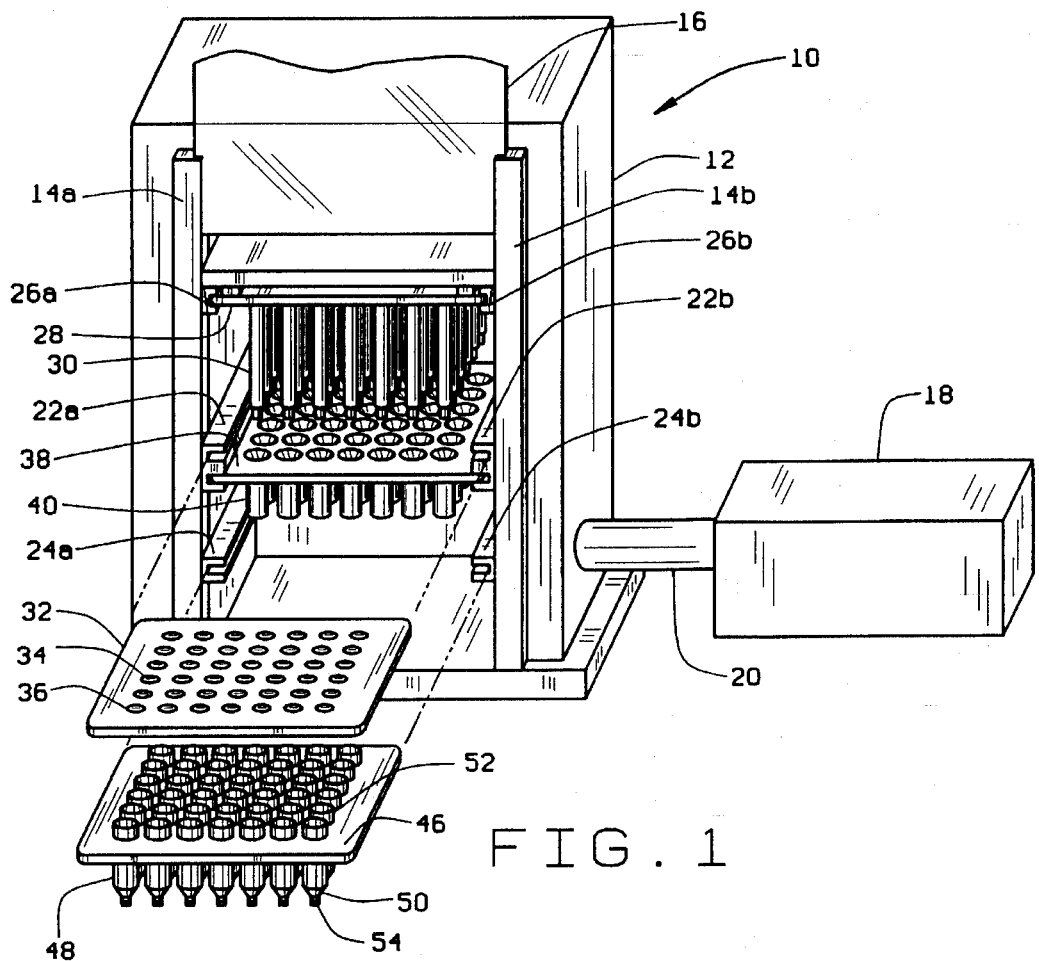
FIG. 1 is a perspective view of an apparatus, shown partially exploded, in which the methods of the invention can be performed.
Figure 2:
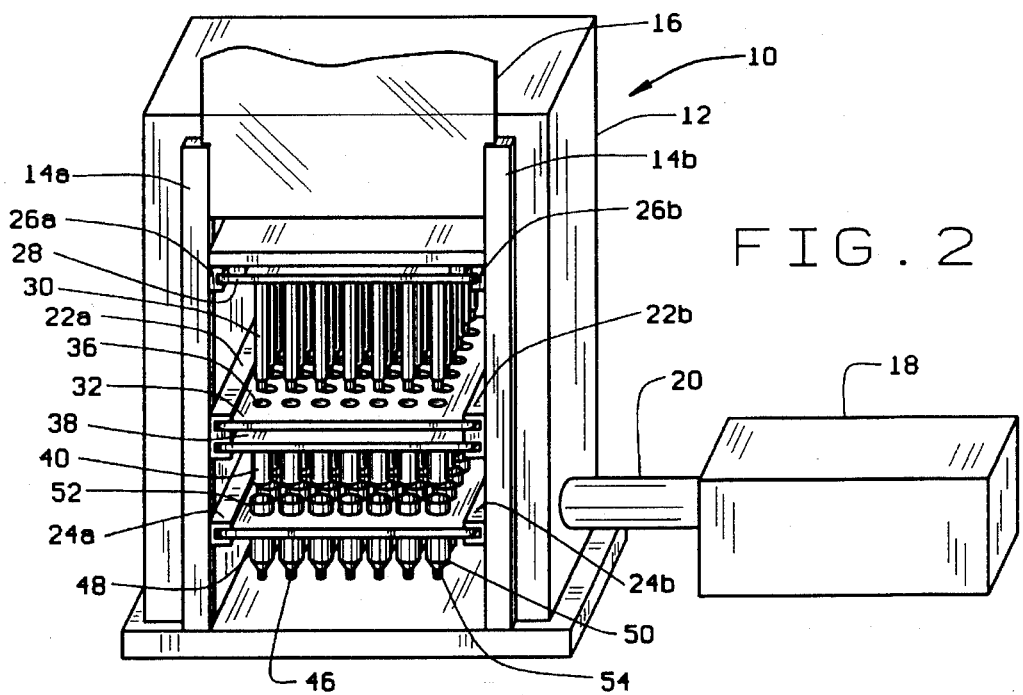
FIG. 2 is a perspective view of an apparatus in which the methods of the invention can be performed.

The methods of the present invention can be performed in any apparatus capable of performing the steps of the invention. Particularly suited for the practice of the methods of the invention is the HYPAK Vent Tube Stopper Placement Unit manufactured by Impro Systems, Inc. for Becton-Dickinson and Company (Franklin Lakes, N.J.). A suitable apparatus is shown in FIGS. 1 and 2 and is generally designated by the numeral 10. The apparatus 10 has an outer housing 12 presenting an interior volume and an access opening on one side to permit access to the interior volume. A pair of guide rails 14a and 14b are provided on opposite sides of the access opening which slidingly receive a panel 16 therein to close access to the interior volume of the housing 12. A pneumatic power means 18 is provided and connected to the interior volume of the housing 12 by means of a conduit 20. Although not shown, the apparatus 10 may be equipped with a means to control the internal atmosphere of the apparatus to have a selected gas atmosphere during the sealing process.

Within the interior volume of the housing 12, plate receiving channel members 22a, 22b, 24a, 24b, 26a and 26b are presented. Channel members 22a and 22b each present two channels therein and channel members 24a, 24b, 26a and 26b each present one channel therein. Each of the channel members are coupled to a mechanism within the housing (not shown) that permits the movement of the channel members, independently or together, vertically up and down within the interior of the housing. The movement of the channel members is achieved by the pneumatic power means 18 and is controlled by a controlling means (not shown). A pin containing plate 28 containing a plurality of pins 30 extending downward from the plate 28 is provided and is slidingly received between plate receiving channel members 26a and 26b. A stopper containing plate 32 which has a plurality of openings 34 therethrough which are of a size suitable to receive a stopper 36 is also provided and is slidingly received between the upper channel in plate receiving channel members 22a and 22b. A reduction tube containing plate 38 having a plurality of reduction tubes 40 extending downwardly therefrom is provided and is slidingly received between the lower channel of plate receiving channel members 22a and 22b. The reduction tubes 40 are best shown in FIGS. 3–7 and each has an upper end 42 of a diameter sufficient to receive a stopper 36 therein without significantly deforming the shape and size of the stopper 36, and a lower end 44 of a diameter less than the diameter of the upper end and less than the diameter of a stopper 36 such that when a stopper 36 is inserted into the lower end of a reduction tube 40, the diameter of the stopper 36 is correspondingly reduced. A syringe containing plate 46 having a plurality of syringes 48 inserted through openings in the syringe containing plate 46 is also provided and is slidingly received between plate receiving channel members 24a and 24b. The syringes 48 are positioned such that the tooled end 50 of the syringe extends downward from the plate 46 and the open end 52 of the syringe is positioned above the top of the plate 46. A sealing means 54 is provided at the tooled end to seal this opening of the syringe.

As shown in FIGS. 1 and 2, the pin containing plate 28 is positioned at the upper end of the housing 12 with the stopper containing plate 32, the reduction tube containing plate 38 and the syringe containing plate 46 positioned below pin containing plate 28, respectively. As also shown in FIG. 1, each of the plates 28, 32, 38, and 46 can be slidingly inserted into its corresponding channel member through the access opening in the housing 12. Thus, plates containing different sizes of the pins 30, stoppers 36, reduction tubes 40 and syringes 48 can be used by inserting them in the respective plate or by inserting a preset plate having the item in the selected size. An apparatus 10 having the plates 28, 32, 38, and 46 in position within the interior volume of the housing 12 and ready for use is shown in FIG. 2.

Referring now to FIGS. 3–7, the operation of the apparatus 10 is shown in partially cut-away, cross-sectional views. In FIGS. 3–7, the syringes 48 are shown filled with a pressure or vacuum sensitive liquid 56, such as a microbubble-based ultrasound contrast media, e.g. Albunex®. Before the apparatus 10 is actuated to seal the pressure or vacuum sensitive liquid 56 in the syringe 48, the apparatus 10 is set up as shown in FIG. 3. The pin containing plate 28 is in its most upward position above stopper containing plate 32. Stoppers 36 are placed in each of the openings 34 in stopper containing plate 32 and the stoppers 36 and the pins 30 aligned accordingly. Reduction tubes 40 are placed in the reduction tube containing plate 38 with the reduced diameter end 44 of the reduction tubes 40 extending downwardly from the plate 38 and the larger diameter upper ends 42 of the reduction tubes 40 aligned with the stoppers 36. Syringes 48 are pre-filled through the open end 52 of the syringe 48 (the tooled end 50 having previously been sealed with a sealing means 54) with the pressure or vacuum sensitive liquid 56 and the syringes 48 are inserted into the openings of syringe containing plate 46 and aligned with the reduction tubes 40. At this time the apparatus is ready to seal the pressure or vacuum sensitive product 56 in the syringes 48 without the use of pressure or vacuum.

The first step is to place the stoppers 36 into the lower end 44 of the reduction tubes 40. This is accomplished by actuating the pneumatic power source 18 to permit downward movement of the pin containing plate 28 and the associated pins 30 to contact the stoppers 36 in stopper containing plate 32 and to push them into the reduction tubes 40 as shown in FIG. 4. It is understood that the stoppers 36 are representative of an elastomeric closure means that is made of a compressible material that permits the reduction in the diameter of the stopper as it is forced by downward pressure from the larger diameter end 42 of the reduction tube 40 into the reduced diameter end 44. The stopper 36 selected to seal the syringe 48 is of a size and diameter that is sufficient to fit into the syringe 48 and effectively seal the pressure or vacuum sensitive liquid therein when the stopper 36 is permitted to expand to its normal diameter.

The next step of the process is best shown in FIG. 5. The reduction tube plate 38 containing the reduction tubes 40 with the stoppers 36 therein are lowered by further downward pneumatic force by the pneumatic power means 18 (and under the control of the controlling mechanism) into the syringes 48. The lower end 44 of the reduction tubes 40 are of an outside diameter slightly less than the inside diameter of the syringe so that the reduction tube 40 is inserted into the syringe 48 without creating any adverse pressure in the syringe. The reduction tubes 40 are lowered into the syringes 48 such that the stopper 36 in the reduction tube 40 is positioned at the selected location in the syringe to effectively seal the pressure or vacuum sensitive liquid 56 therein and to reduce the amount of headspace between the stopper 36 and the top of the liquid. It is to be noted that in this step of the process the pin 30 remains in contact with the stopper 36. After the stopper 36 is placed at the selected location in the syringe 48, the reduction tube containing plate 38 and the reduction tube 40 therein are retracted in a manner removing the reduction tube 40 from the syringe 48, while the downward pressure exerted by the pin 30 continues to be exerted on the stopper 36. As the reduction tube 40 moves upward out of the syringe 48, the stopper 36 remains in the syringe and expands to its normal diameter against the inner diameter of the syringe 48 thereby sealing the pressure or vacuum sensitive liquid 56 therein. The final step in the process is the upward movement of the pin 30 withdrawing its contact with the stopper 36.

The following Example describes a preferred embodiment of the invention. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims.

EXAMPLE 1

This Example is provided to illustrate the method of this invention.

A HYPAK Vent Tube Stopper Placement Unit was setup to provide an acceptable headspace within the assembled syringe and to prevent exposure of the product to damaging pressures by adjusting the pin containing plate, the stopper containing plate and the reduction tube containing plate. Exhaust valves on the pneumatic actuators were adjusted to control acceleration and deceleration of the reduction tubes during stopper placement. The pneumatic input to the apparatus was connected to a 60 psig regulated source of medical grade nitrogen.

The contents of 10 ml vials of Albunex® were poured into 10 ml syringe barrels using a small glass funnel. The syringe barrels had a tip cap to seal the tooled end. These syringe barrels were placed in the apparatus and stoppers were placed in the stopper containing plate. The stoppers were Teflon® faced siliconized stoppers molded from gray butyl rubber. The door was closed on the apparatus to initiate placement of the pistons in the syringe barrels. The apparatus was actuated and the pistons were placed in the diameter reduction tubes by the pins. The diameter reduction tube plate was then lowered to precisely position the piston within the barrel and the placement pin maintained the position of the piston as the diameter reduction tube was retracted. As the tube retracted, the piston expanded against the inner diameter of the barrel and the placement pin was withdrawn. The syringes were then removed and placed in storage. The Albunex® filled syringes were subsequently analyzed and determined that the functionality of the product was not adversely affected by the sealing process.

What is claimed is:

1. A method for packaging a pressure or vacuum sensitive product in a container to seal the product therein, the container having first and second ends, the method comprising:

sealing one of the ends of the container;

introducing the pressure or vacuum sensitive product into the container through the other end;

inserting a compressible closure member of a normal diameter sufficient to sealingly engage the inner wall of the container into a generally conical hollow tube, the generally conical hollow tube having a first end of a diameter permitting the insertion of the compressible closure member therein and a second end of a diameter less than the diameter of the first end, such that the closure member is positioned generally within the second end of the tube and the diameter of the closure member positioned therein is correspondingly reduced;

inserting the tube containing the closure member into the container to position the closure member at a selected location within the container;

providing a means for holding the position of the closure member substantially stationary with respect to the tube at the selected location relative to the container;

withdrawing the tube from the container in a manner placing the closure member in the container such that the closure member expands and sealingly engages the inner wall of the container; and removing the means for holding the closure member.

2. The method of claim 1 wherein the container is a single compartment syringe.

3. The method of claim 2 wherein the pressure or vacuum sensitive product is a liquid.

4. The method of claim 3 wherein the pressure or vacuum sensitive product is comprised of microbubbles or gas-filled encapsulated microspheres.

5. The method of claim 4 wherein the pressure or vacuum sensitive product is an ultrasound contrast agent.

6. The method of claim 5 wherein the pressure or vacuum sensitive product is an albumin based microbubble.

7. The method of claim 5 wherein the pressure or vacuum sensitive product is a surfactant-based, gas-filled microbubble.

8. The method of claim 5 wherein the pressure or vacuum sensitive product is a polymer-based, gas-filled microbubble.

9. The method of claim 5 wherein the pressure or vacuum sensitive product is a liposome-based, gas-filled microbubble.

10. The method of claim 5 wherein the pressure or vacuum sensitive product is a phospholipid-based, gas-filled microbubble.

11. A method for sealing a pressure or vacuum sensitive product in a container, the container having at least one sealed end, the method comprising:

introducing the pressure or vacuum sensitive product into the container;

inserting a compressible closure member of a diameter sufficient to sealingly engage the inner wall of the container into a generally conical hollow tube, the generally conical hollow tube having a wide end of a diameter substantially the same as the diameter of the closure member and a reduced end of a diameter less than the diameter of the container, such that the closure member is positioned generally within the reduced end of the tube and the diameter of the closure member is correspondingly reduced;

inserting the tube containing the closure member into the container in a manner positioning the closure member at a selected location in the container;

providing a means for holding the position of the closure member substantially stationary with respect to the tube at the selected location relative to the container;

retracting the tube from the container in a manner leaving the closure member in the container such that the closure member expands and sealingly engages the inner wall of the container; and retracting the means for holding the closure member.

12. The method of claim 11 wherein the container is a single compartment syringe.

13. The method of claim 12 wherein the pressure or vacuum sensitive product is a liquid.

14. The method of claim 13 wherein the pressure or vacuum sensitive product is comprised of microbubbles or gas-filled encapsulated microspheres.

15. The method of claim 14 wherein the pressure or vacuum sensitive product is an ultrasound contrast agent.

16. The method of claim 15 wherein the pressure or vacuum sensitive product is an albumin based microbubble.

17. The method of claim 15 wherein the pressure or vacuum sensitive product is a surfactant-based, gas-filled microbubble.

18. The method of claim 15 wherein the pressure or vacuum sensitive product is a polymer-based, gas-filled microbubble.

19. The method of claim 15 wherein the pressure or vacuum sensitive product is a liposome-based, gas-filled microbubble.

20. The method of claim 15 wherein the pressure or vacuum sensitive product is a phospholipid-based, gas-filled microbubble.

* * * * *